(12) United States Patent
Morris et al.

(10) Patent No.: US 8,951,165 B2
(45) Date of Patent: Feb. 10, 2015

(54) PERSONAL TRAINING WITH PHYSICAL ACTIVITY MONITORING DEVICE

(71) Applicant: Microsoft Corporation, Redmond, WA (US)

(72) Inventors: Daniel Morris, Bellevue, WA (US); Ilya Kelner, Redmond, WA (US); Farah Shariff, Kirkland, WA (US); Dennis Tom, Redmond, WA (US); T. Scott Saponas, Woodinville, WA (US); Andrew Guillory, Seattle, WA (US)

(73) Assignee: Microsoft Corporation, Redmond, WA (US)

( * ) Notice: Subject to any disclaimer, the term of this patent is extended or adjusted under 35 U.S.C. 154(b) by 31 days.

(21) Appl. No.: 13/785,322

(22) Filed: Mar. 5, 2013

(65) Prior Publication Data

US 2014/0257535 A1  Sep. 11, 2014

(51) Int. Cl.
| | |
|---|---|
| A63B 21/00 | (2006.01) |
| G06F 19/00 | (2011.01) |
| A63B 24/00 | (2006.01) |
| A61B 5/11 | (2006.01) |
| A61B 5/00 | (2006.01) |
| A63B 71/06 | (2006.01) |

(52) U.S. Cl.
CPC .............. *A63B 24/00* (2013.01); *A61B 5/1118* (2013.01); *A61B 5/1123* (2013.01); *A63B 24/0062* (2013.01); *A63B 24/0075* (2013.01); *G06F 19/3481* (2013.01); *A61B 5/6824* (2013.01); *A63B 2024/0068* (2013.01); *A63B 2071/0663* (2013.01); *A63B 2220/17* (2013.01)
USPC .......................... 482/8; 482/9; 700/91; 706/46

(58) Field of Classification Search
None
See application file for complete search history.

(56) References Cited

U.S. PATENT DOCUMENTS

| | | |
|---|---|---|
| 6,171,218 B1 | 1/2001 | Shea |
| 8,132,229 B2 | 3/2012 | Garbow et al. |
| 8,221,290 B2 | 7/2012 | Vincent et al. |
| 8,235,815 B1 | 8/2012 | Kavars et al. |
| 8,260,667 B2 | 9/2012 | Graham et al. |
| 8,287,436 B2 | 10/2012 | Shum et al. |
| 2005/0227811 A1 | 10/2005 | Shum et al. |

(Continued)

FOREIGN PATENT DOCUMENTS

| | | |
|---|---|---|
| EP | 1821309 A1 | 8/2007 |
| EP | 2330554 A1 | 8/2011 |

(Continued)

OTHER PUBLICATIONS

"EA Sports Active 2", Retrieved at <<http://www.ea.com/ea-sports-active-2>>, Jul. 17, 2011, pp. 10.

(Continued)

*Primary Examiner* — Dmitry Suhol
*Assistant Examiner* — Jason Yen
(74) *Attorney, Agent, or Firm* — Brandon Roper; Judy Yee; Micky Minhas

(57) ABSTRACT

A physical activity monitoring device receives a workout regimen including a plurality of exercises. For each of the plurality of exercises, the physical activity monitoring device indicates that exercise to a user and measures physical activity attributes of the user. The physical activity monitoring device outputs information regarding the user's progress towards completion of that exercise based on the physical activity attributes.

16 Claims, 8 Drawing Sheets

(56) References Cited

U.S. PATENT DOCUMENTS

| | | | |
|---|---|---|---|
| 2007/0017967 | A1 | 1/2007 | Bhavnani |
| 2007/0060446 | A1 | 3/2007 | Asukai et al. |
| 2007/0111858 | A1 | 5/2007 | Dugan |
| 2007/0123754 | A1 | 5/2007 | Cuddihy et al. |
| 2007/0169614 | A1 | 7/2007 | Sasaki et al. |
| 2008/0090703 | A1* | 4/2008 | Rosenberg ............ 482/8 |
| 2008/0096726 | A1 | 4/2008 | Riley et al. |
| 2008/0162088 | A1 | 7/2008 | DeVaul et al. |
| 2008/0171636 | A1 | 7/2008 | Usui et al. |
| 2008/0255800 | A1 | 10/2008 | Meriheina et al. |
| 2009/0075781 | A1* | 3/2009 | Schwarzberg et al. ...... 482/8 |
| 2009/0174558 | A1 | 7/2009 | White |
| 2010/0009810 | A1 | 1/2010 | Trzecieski |
| 2010/0167801 | A1* | 7/2010 | Karkanias et al. ............ 463/7 |
| 2010/0197463 | A1* | 8/2010 | Haughay et al. ............ 482/8 |
| 2010/0204952 | A1 | 8/2010 | Irlam et al. |
| 2011/0092337 | A1 | 4/2011 | Srinivasan et al. |
| 2011/0137836 | A1 | 6/2011 | Kuriyama et al. |
| 2012/0021644 | A1 | 1/2012 | Osaki |
| 2012/0046901 | A1 | 2/2012 | Green et al. |
| 2012/0214644 | A1 | 8/2012 | Sasaki |
| 2012/0244995 | A1 | 9/2012 | Dibenedetto et al. |
| 2013/0035209 | A1 | 2/2013 | Gilley et al. |
| 2013/0052620 | A1 | 2/2013 | Franklin et al. |
| 2013/0054505 | A1* | 2/2013 | Ross et al. ............ 706/46 |
| 2013/0123955 | A1 | 5/2013 | Greenberg et al. |
| 2013/0162427 | A1 | 6/2013 | Dibenedetto et al. |
| 2013/0190903 | A1 | 7/2013 | Balakrishnan et al. |
| 2013/0196821 | A1* | 8/2013 | Watterson et al. ............ 482/9 |
| 2014/0074262 | A1* | 3/2014 | Pelosi ............ 700/91 |
| 2014/0074431 | A1 | 3/2014 | Modi |

FOREIGN PATENT DOCUMENTS

| | | |
|---|---|---|
| EP | 2407218 A2 | 1/2012 |
| WO | 2010096691 A3 | 8/2010 |

OTHER PUBLICATIONS

"Manage your Fitness on Xbox 360 information and privacy settings", Retrieved at <<http://support.xbox.com/en-US/apps/fitness/manage-your-information-and-privacy-settings>>, Retrieved Date: Nov. 20, 2012, pp. 3.

"How to download workouts/race plans into your Garmin Forerunner/Edge", Retrieved at <<http://www.dcrainmaker.com/2008/09/how-to-download-workoutsrace-plans-into.html>>, Sep. 24, 2008, pp. 6.

"Motoactv", Retrieved at <<https://motorola-global-portal.custhelp.com/ci/fattach/get/429626/1336753328/redirect/1/session/L2F2LzEvdGItZS8xMzUzMzg0NDIxL3NpZC9JRG9XMkpibA==/filename/Motoactv_GSG_US_68016468001D.pdf>>, Retrieved Date : Nov. 19, 2012, pp. 2.

"Joule 3.0", Retrieved at <<http://www.cycleops.com/products/cycling-computers.html?page=shop.product_details&flypage=flypage.images.tpl&product_id=24&category_id=1>>, Sep. 18, 2010, pp. 5.

European Patent Office, International Search Report and Written Opinion of PCT/US2014/020194, May 26, 2014, 12 pages.

European Patent Office, International Search Report and Written Opinion of PCT/US2014/020190, Jun. 12, 2014, 8 pages.

European Patent Office, International Search Report and Written Opinion of PCT/US2014/020352, Jun. 24, 2014, 13 pages.

Bao, Ling., "Physical Activity Recognition from Acceleration Data under Semi-Naturalistic Conditions", Massachusetts Institute of Technology, Aug. 2003, 89 pages.

Striiv, Why Striiv Works, http://www.striiv.com/products/how-it-works/, Dec. 14, 2012, 2 pages.

Alan Henry, "Five Best Fitness Tracking Appliances", http://lifehacker.com/5907870/five-best-fitness-tracking-appliances, May 6, 2012, 11 pages.

* cited by examiner

PERSONAL TRAINING WITH PHYSICAL ACTIVITY MONITORING DEVICE

BACKGROUND

Exercise and other physical activities can be very beneficial to a person's health and wellbeing. Some people utilize personal trainers to enhance health and wellbeing through structured exercise regimens. However, not everybody can afford a personal trainer. Even people that frequently train with a personal trainer are unlikely to have access to the personal trainer at all times when physical activities are performed.

SUMMARY

A physical activity monitoring device receives a workout regimen including a plurality of exercises. For each of the plurality of exercises, the physical activity monitoring device indicates that exercise to a user and measures physical activity attributes of the user. The physical activity monitoring device outputs information regarding the user's progress towards completion of that exercise based on the physical activity attributes.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

This disclosure is directed to a physical activity monitoring device (PAMD) that may be used to augment a gaming experience and/or to receive and monitor a workout regimen.

In a workout, an individual may spend time performing physical activities or exercises as well as time spent recovering from the activities, time spent preparing for the activities, and time spent performing non-exercise activity, such as drinking water. In order for the PAMD to recognize and distinguish physical activities or exercises performed by a user wearing the PAMD, it may first distinguish between times of actual exercise and non-exercise activities. In some embodiments, the PAMD samples user movements with a sensor array including one or more sensors configured to measure physical activity attributes of a user wearing the PAMD. The sampled data may then be segmented into periods of exercise and periods of non-exercise. Within the periods of exercise, the PAMD may then be trained to uniquely identify patterns in the sampled data that are representative of specific physical activities or exercises, thereby recognizing the physical activity or exercise performed by the user wearing the PAMD. For repetitive physical activities or exercises, the PAMD may then count the number of repetitions of the given repetitive physical activity or exercise performed by the user wearing the PAMD.

Figure 1:
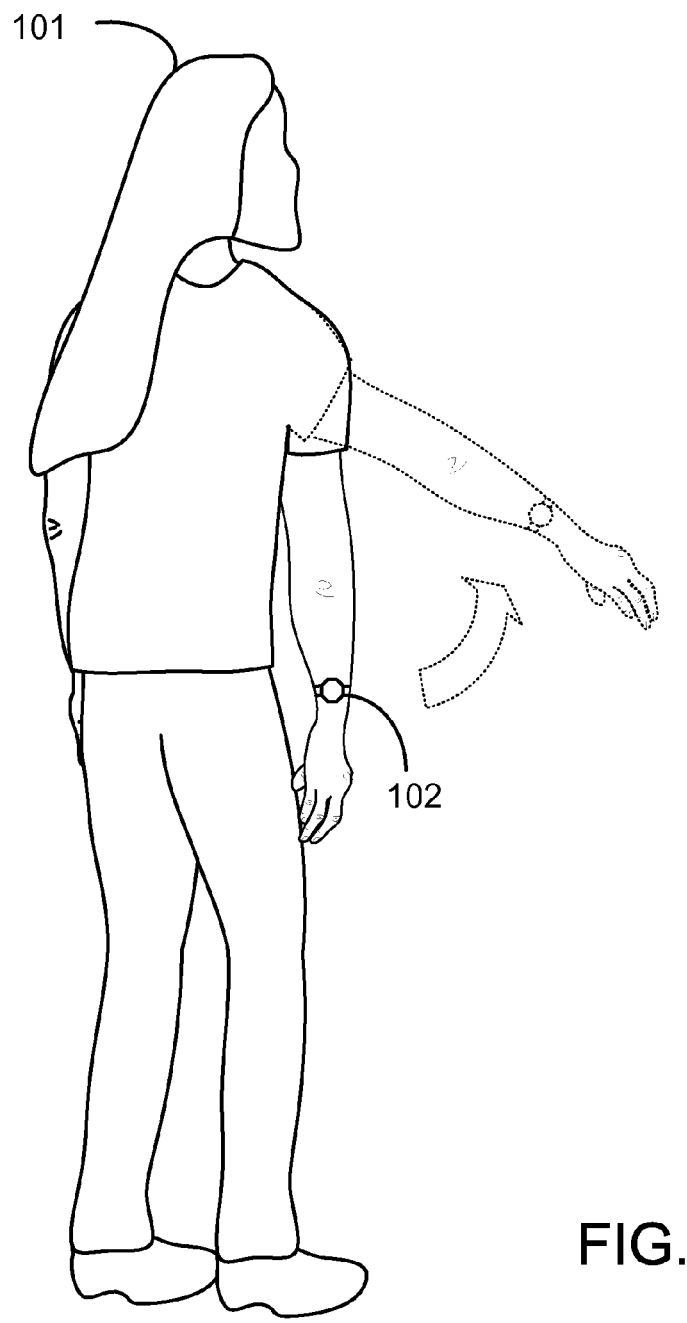
FIG. 1 shows a user wearing a physical activity monitoring device in accordance with an embodiment of the present disclosure.

FIG. 1 shows a user 101 wearing a physical activity monitoring device 102 in accordance with the present disclosure. In some embodiments, PAMD 102 may be in the form of a wearable arm band. PAMD 102 may be worn by user 101 while user 101 is exercising or otherwise performing a specific physical activity. PAMD 102 may employ a method of smart activity analysis. Smart activity analysis may allow for the PAMD to recognize and distinguish physical activities or exercises performed by a user wearing the PAMD, and further may allow for the PAMD to count the repetitions of a physical activity or exercise performed by a user wearing the PAMD.

Figure 2:
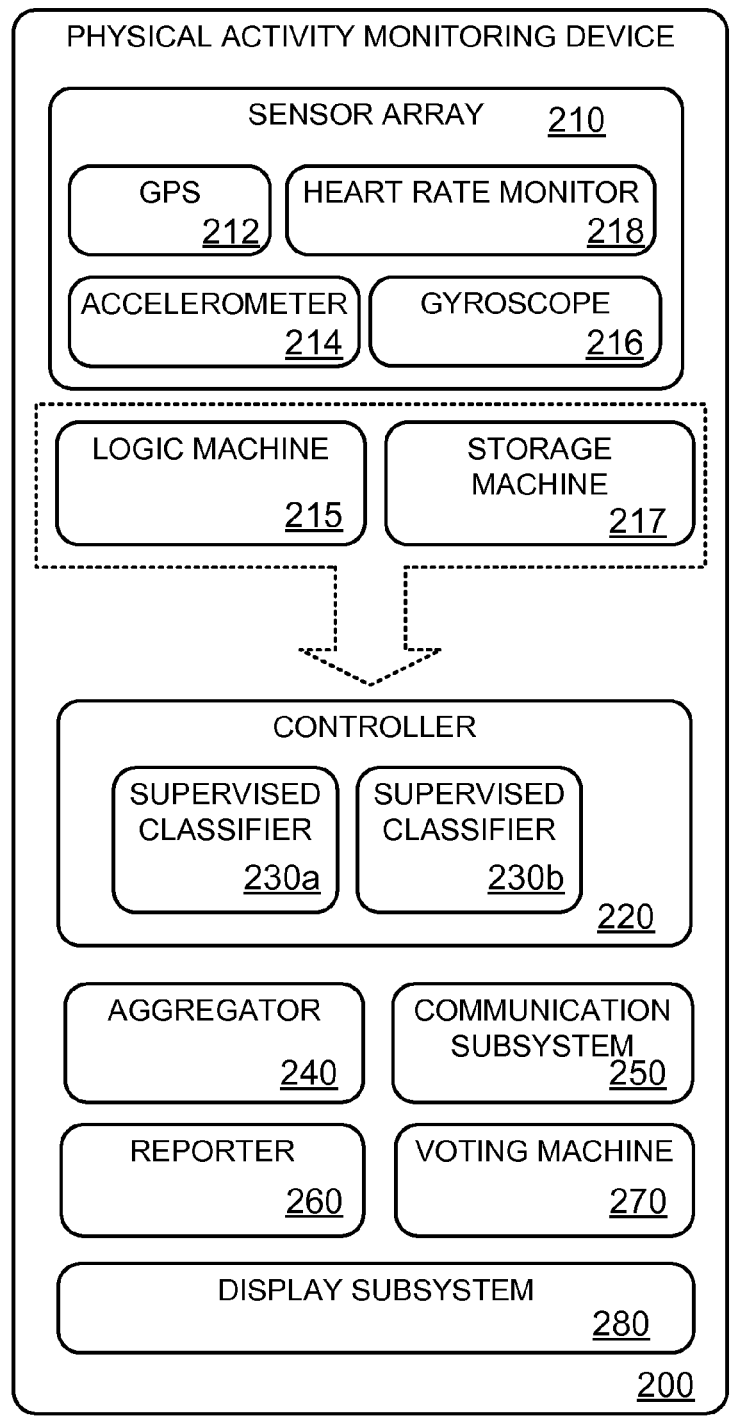
FIG. 2 shows a physical activity monitoring device in accordance with an embodiment of the present disclosure.

FIG. 2 schematically shows a physical activity monitoring device 200 in accordance with the present disclosure. PAMD 200 may include sensor array 210, logic machine 215, storage machine 217, controller 220, supervised classifier 230a, supervised classifier 230b, aggregator 240, communication subsystem 250, reporter 260, voting machine 270 and display subsystem 280.

Sensor array 210 may include one or more sensors, such as accelerometer 214, GPS 212, gyroscope 216, heart rate monitor 218, and/or other suitable sensors. Data from sensor array 210 may allow the device to automatically distinguish between different physical activities or exercises performed by the user wearing the PAMD. In some examples, accelerometer 214 may sample user movements at a fixed sampling rate. The sampling may occur at a sample rate of 25 Hz, or another suitable sampling rate, such as 50 Hz. Data from GPS 212 may be used to learn the speed of the user performing a physical activity or exercise outdoors. For example, the GPS derived data may be used to distinguish between periods of running, walking and biking. Furthermore, the GPS may be used to assess a user's location. Such location information may be used to distinguish activities. For example, a user is likely to be playing tennis when on a tennis court or golfing when on a golf course. In concert with data received from the accelerometer, the GPS data may be used to calibrate the user's stride. This information may be stored and used to distinguish and calibrate the same physical activities or exercises when performed indoors or when GPS data is otherwise unavailable, allowing for accurate distance and pace information to be calculated in the absence of GPS data.

Accelerometer 214 optionally may be a 3-axis accelerometer. Data received from accelerometer 214 may be used to detect variations in patterns for different repetitive physical activities or exercises that may include pushups, situps, squats, etc. The repeatability of the signals for such repetitive physical activities or exercises may be used to detect the repetitions of these and similar exercises. Data received from accelerometer 214 may also be used to detect variations in patterns for different static physical activities or exercises that may include wall squats, planks, yoga poses, etc.

For distance based activities, PAMD 200 may further detect and distinguish between varying speeds of movement, including walking, jogging, fast jogging, and running. This may be accomplished by measuring the speed of the user's footfall with accelerometer 214. This data may then be used to dynamically adjust the distance calculation specific to the activity. For example, the number of steps taken by a user while walking may equate to a shorter distance than for the same number of steps taken by the same user while running. Over numerous periods of physical activity or exercise, the user's true stride length for walking, jogging, running, etc. may be learned using data from GPS 212 and accelerometer 214.

PAMD 200 may further include controller 220, which optionally may be instantiated via use of logic machine 215 and storage machine 217. Controller 220 may be configured to automatically determine time intervals where the user is actively engaged in a physical activity based on the physical activity attributes. This process may also be referred to herein as segmentation. In one example, PAMD 200 may indicate that the user is to perform jumping jacks as an exercise. Following this indication, the user may take time to prepare for the exercise, for example walking around a room, taking a drink of water, or getting in position to begin the jumping jacks. The process of segmentation may separate periods of actual exercise from other activities not related to the physical activity or exercise. Removing periods of non-exercise from the analysis may lessen the possibility of PAMD 200 counting false repetitions. Similarly, PAMD 200 may be able to more accurately determine which physical activity or exercise a user is engaged in if the recognition system only analyzes data from periods of time when the user is actively engaged in the physical activity or exercise.

In one example, PAMD 200 may indicate that a user is to perform a time based activity, for example pushups for 30 seconds. PAMD 200 may more accurately track the 30 seconds of pushups if it does not begin evaluating the user's physical activity attributes during the time the user is getting into position to perform the pushups. By accurately determining when the user is performing pushups, PAMD 200 may be able to make accurate claims about user biometrics, for example, how many calories the user burned while performing the pushups.

PAMD 200 may be trained through machine learning to recognize periods where the user is actively engaged in a physical activity or exercise. This process of segmentation may be further broken down into sub-processes of preprocessing, feature computation, classification, and aggregation.

Figure 3:
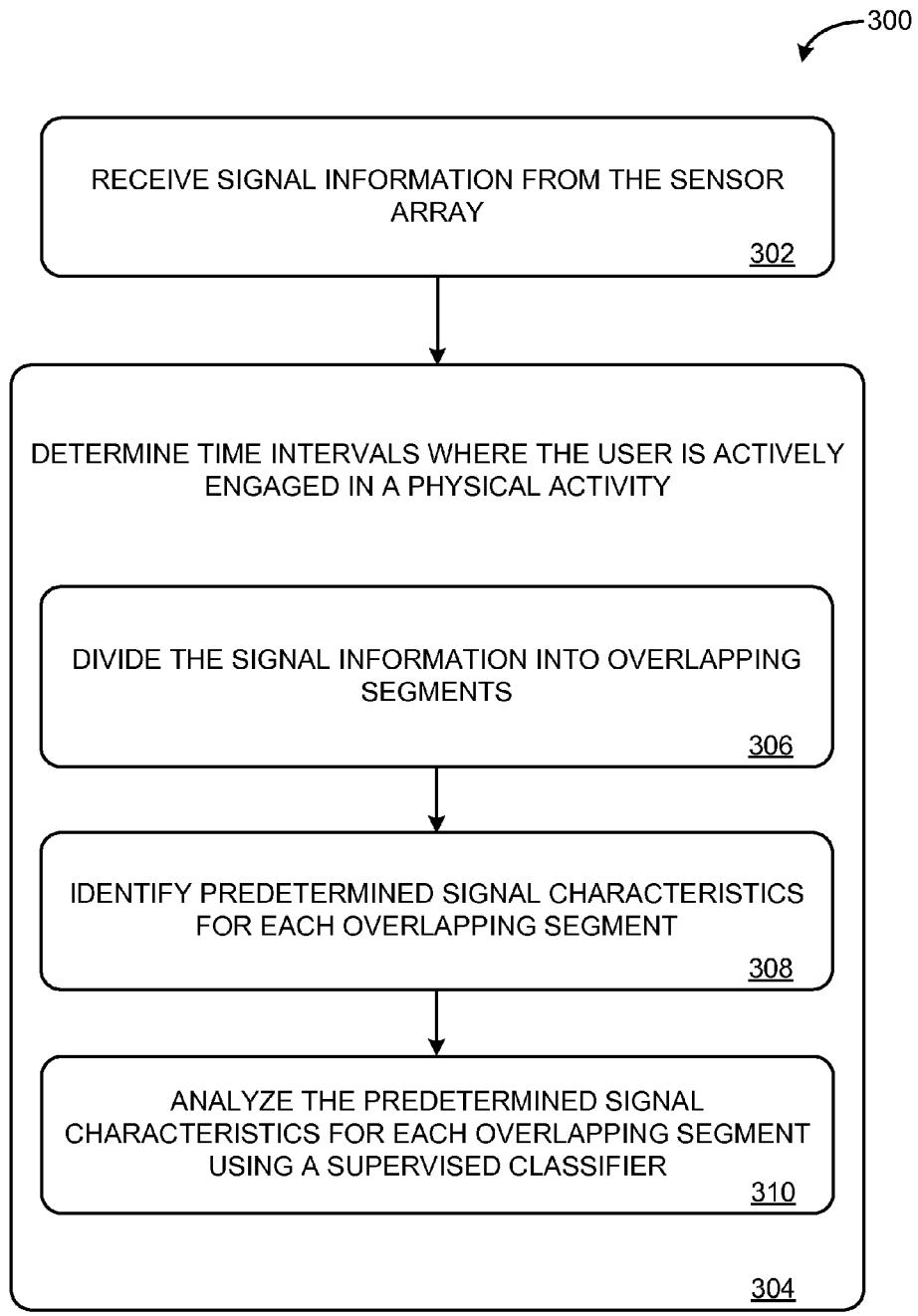
FIG. 3 shows an example method of determining periods in which a user is actively engaged in a physical activity in accordance with an embodiment of the present disclosure.

FIG. 3 shows an example method 300 that may be used by controller 220 to determine periods where the user is actively engaged in a physical activity. At 302, method 300 includes receiving signal information from a sensor array (e.g., sensor array 210). Such signal information may be received by controller 220, for example. The signal information is representative of the physical activity attributes of the user. In some examples, this signal information may include raw data from accelerometer 214 or gyroscope 216. Accelerometer 214 and gyroscope 216 may each output three raw signals, giving a total of six raw input signals. The raw input signals may then be run through a low-pass filter, the output of which may then be six smoothed signals.

At 304, method 300 may include determining time intervals where the user is actively engaged in a physical activity. For example, controller 220 may use the signal information received at 302 as the basis for determining time intervals. As shown in FIG. 3, the process of determining time intervals may include a plurality of sub-processes. Nonlimiting examples of such sub-processes are provided below. However, it should be understood that time intervals of active engagement may be determined in any suitable manner without departing from the scope of this disclosure.

At 306, method 300 may include dividing the signal information into overlapping segments. In one example, the data may be divided into windows with a length of five seconds. Each window may be advanced by 200 ms from the previous window, such that each five second window shares 4.8 seconds of data with the previous and following windows.

At 308, method 300 may include identifying predetermined signal characteristics (e.g., acceleration characteristics of acceleration information measured by an accelerometer of the sensor array) for each overlapping segment. In some examples, controller 220 may transform each five second window of smoothed data into 200 signal characteristics that are then used to characterize the physical activity or exercise, but there may be fewer or greater signal characteristics. In one example, the six smoothed signals may be transformed into ten output signals. The ten output signals in this example may include smoothed accelerometer data in the x, y and z axes, smoothed gyroscope data in the x, y and z axes, the magnitude of the accelerometer signal at each sample, the magnitude of the gyroscope signal at each sample, the projection of the three-dimensional accelerometer signal onto the first principal component of that signal, projection of accelerometer signals in the y and z axes onto their own principal component, and the projection of the three-dimensional gyroscope signal onto the first principal component of that signal.

The output signals may be selected based on characteristics of the PAMD. In some embodiments where the signal information includes signals in three dimensions, signals in two of the three dimensions may be dimensionally reduced into a signal in one dimension. For example, if the PAMD is configured as a device that adheres to the body of the user or otherwise is configured to be fixed to the body of the user, the smoothed data in the x, y and z axes may be considered to accurately reflect the movement of the user in these three axes. However, if the PAMD is configured as a wearable arm-band, for example, the PAMD may be subject to accidental rotation about the arm or wrist of the user. In this example, data in the x-axis (e.g. along the arm of the user) may be considered to accurately reflect the movement of the user in the x-axis, but data in the y and z axes could represent movement in a plurality of axes, depending on the position of the PAMD. In this example, the projection of accelerometer signals in the y and z axes on their own principal components may be selected as output signals. By reducing the dimensionality of signals in the y and z axes, rotation of the PAMD about the arm of the user may be accounted for by compressing the unknown axes into a more predictable signal.

For each of these output signals, controller 220 may then calculate 20 signal characteristics for each output signal. Controller 220 may also calculate a greater or lesser number of signal characteristics. In some examples, the signal characteristics may include a number of autocorrelation peaks, a number of negative autocorrelation peaks, a maximum autocorrelation value, a log of a maximum autocorrelation value, a root-mean-square amplitude, a mean, a standard deviation, a variance, and an integrated root-mean-square amplitude. The signal characteristics may also include a number of strong peaks, where strong peaks may be defined as the number of autocorrelation peaks that are larger than their neighboring peaks by a threshold and are more than a threshold lag away from their neighboring peaks. The signal characteristics may also include a number of weak peaks, where weak peaks may be defined as the number of autocorrelation peaks that are within a threshold height of their neighboring peaks and are less than a threshold lag away from their neighboring peaks. The signal characteristics may further include the value of the first autocorrelation peak after a zero-crossing, local non-linearity or other measures of how well a best-fit line explains the data, and a set of power bands, where a magnitude is calculated for the power spectrum in each selected band spread over the range of frequencies that can be obtained by the sensor array. In this example, seven power bands may be calculated, but there may be more or fewer power bands, for example ten power bands.

Additional signal characteristics may be calculated for each signal. For each five second window, the signal characteristics may give an indication of the autocorrelation of the signal, in other words, an indication of how repetitive or self-similar the data is. Signals from time periods where the user is exercising may be more repetitive than signals from time periods where the user is not exercising. In some examples, signals from time periods where the user is engaged in fast motions may be more likely to correspond to exercise than non-exercise.

At 310, method 300 may include analyzing the predetermined signal characteristics for each overlapping segment using a supervised classifier. As shown in FIG. 2, controller 220 may include supervised classifier 230a. Supervised classifier 230a may be trained to recognize if the user is actively engaged in a physical activity during the overlapping segment. In general, supervised classifier 230a and/or other aspects of controller 220 may be trained through a machine-learning process to recognize signal characteristics that are representative of a user being actively engaged in a physical activity or exercise and to further recognize signal characteristics that are representative of a user not being actively engaged in a physical activity or exercise.

In one example, supervised classifier 230a utilizes a support vector machine (SVM), for example a linear support vector machine. In some examples supervised classifier 230a utilizes a machine-learning decision tree. In some examples where supervised classifier 230a utilizes an SVM, the SVM may be configured to generate a vector of numbers, and further configured to multiply the predetermined signal characteristics by the vector of numbers to obtain a plurality of multiplication products. The SVM may be further configured to compare the multiplication products to a threshold or thresholds determined through machine learning as described above. The SVM may then be configured to classify a value above the threshold as representative of an overlapping segment wherein the user is actively engaged in a physical activity and classify a value below the threshold as representative of an overlapping segment wherein the user is not actively engaged in a physical activity.

In some examples where supervised classifier 230a includes an SVM, analyzing the predetermined signal characteristics may include training the support vector machine with data collected from a plurality of users during time intervals where the users were actively engaged in a physical activity or exercise and time intervals where the users were not actively engaged in a physical activity or exercise. Analyzing the predetermined signal characteristics may further include generating a set of transformation vectors, a weight vector and a threshold representative of a user actively engaged in a physical activity or exercise, followed by multiplying the predetermined signal characteristics by the set of transformation vectors and weight vector to obtain a plurality of multiplication products. Analyzing the predetermined signal characteristics may further include comparing the multiplication products to the threshold, classifying a value above the threshold as representative of an overlapping segment wherein the user is actively engaged in a physical activity or exercise; and classifying a value below the threshold as representative of an overlapping segment wherein the user is not actively engaged in a physical activity or exercise.

When supervised classifier 230a has classified each overlapping segment, PAMD 200 may formulate a single best guess as to whether the user is actively engaged in a physical activity or exercise during each 5-second window.

As shown in FIG. 2, PAMD 200 may further include aggregator 240 configured to determine a time interval defined by a plurality of the classified overlapping segments where the user is likely to be actively engaged in a physical activity. In other words, aggregator 240 may improve accuracy of supervised classifier 230a, or analyze groups of overlapping segments to determine longer time intervals that are representative of exercise or non-exercise.

Predictions made by supervised classifier 230a may occasionally flip back and forth. In one example, a user may be standing still for a period of time, and some overlapping segments may be classified as representative of the user being engaged in a physical activity or exercise. The reverse may also take place—a user may be exercising for a period of time and some overlapping segments within that period may be classified as representative of non-exercise. In some examples, a user may pause to catch their breath in the middle of an exercise; however, overlapping segments on either side of the pause are actually representative of the same physical activity or exercise. In an example where the user pauses to catch their breath in the middle of a repetitive activity, repetitions on both sides of the pause should be counted towards the same total number of repetitions. In this manner, aggregator 240 may fix the output of the classifier to output useable time intervals where the user is engaged in a physical activity or exercise.

Figure 4:
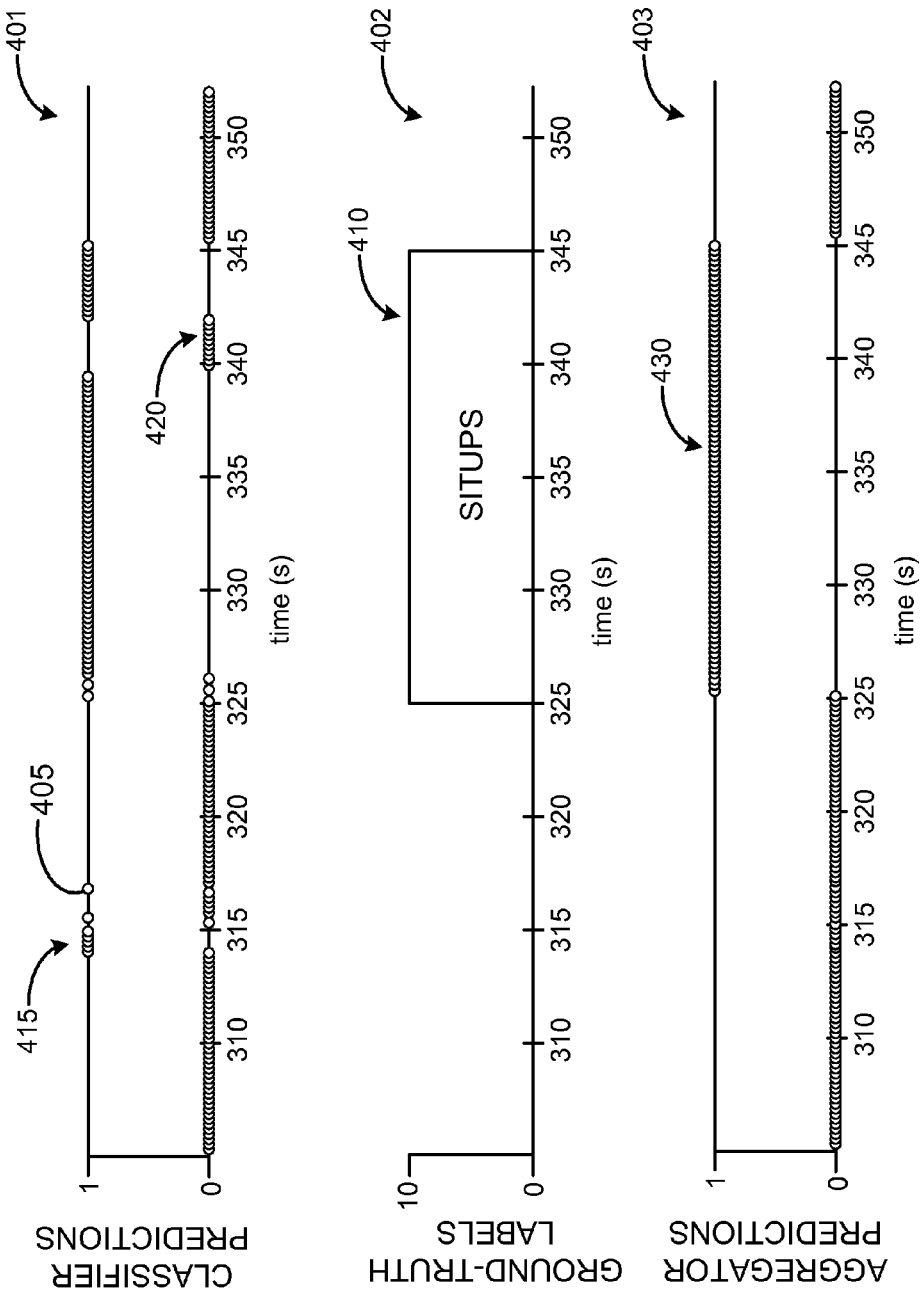
FIG. 4 shows analysis of an example segment of a workout regimen in accordance with an embodiment of the present disclosure.

An example of aggregator 240 fixing the output of supervised classifier 230a is shown in FIG. 4. FIG. 4 shows an example of a segment of physical activity that may be part of a workout regimen. Graph 401 shows the output of supervised classifier 230a for a time interval spanning approximately 1 minute. Each plot point 405 represents one overlapping segment. Each overlapping segment may be given a value of 1 (classified as "exercise") or 0 (classified as "non-exercise"). Graph 402 shows the actual activity of a user. As shown at 410, the user performed sit ups for a period of 20 seconds. However, as shown at 415, some overlapping segments may be initially classified as "exercise", even when the user was not actively engaged in a physical activity or exercise. Similarly, as shown at 420, some overlapping segments may be classified as "non-exercise", even when the user was actively engaged in a physical activity or exercise. As shown in graph 403, aggregator 240 may fix the output of the classifier to output useable time intervals where the user is engaged in a physical activity or exercise, such as time interval 430.

Aggregator 240 may employ one or more methods to analyze the classification of overlapping segments and output a time interval where the user is likely to be engaged in a physical activity or exercise. In one example, aggregator 240 uses a process of streak-based aggregation. In this example, aggregator 240 starts by assuming a non-exercise state and proceeds to analyze the overlapping segments in sequence. If a predetermined number ($k_1$) of overlapping segments are classified as "exercise", aggregator 240 may switch to assuming an exercise state, beginning from the first of the $k_1$ overlapping segments. In one example, $k_1$ may be set to fifteen overlapping segments. In other words, if fifteen consecutive overlapping segments are classified as "exercise", aggregator 240 switches to assume an exercise state. Another predetermined number ($k_2$) which may or may not be equal to $k_1$ may be utilized to indicate aggregator 240 should switch from assuming an exercise state to assuming a non-exercise state.

In some examples, aggregator 240 uses a process of percent-based aggregation. In this example, aggregator 240 starts by assuming a non-exercise state and analyzes the overlapping segments in sequence. If a predetermined percentage ($p_1$%) of overlapping segments is classified as "exercise" over a predetermined time interval (t), aggregator 240 may switch to assuming an exercise state, beginning from the first of the overlapping segments classified as "exercise". For example, $p_1$ may equal 75 and t may be equal to 10, thus when 75% of overlapping segments over 10 seconds are classified as "exercise", aggregator 240 may switch to assuming an exercise state, beginning from the first of the overlapping segments classified as "exercise". Another predetermined percentage ($p_2$%) which may or may not be equal to $p_1$% may be utilized to indicate aggregator 240 should switch from assuming an exercise state to assuming a non-exercise state.

In some examples, aggregator 240 uses a process of accumulator-based aggregation. In this example, aggregator 240 starts by assuming a non-exercise state and analyzes the overlapping segments in sequence. Each overlapping segment that is classified as "exercise" adds a point to a subtotal. When the subtotal exceeds a predetermined threshold ($a_1$) aggregator 240 switches to assume an exercise state. Another predetermined threshold ($a_2$) which may or may not be equal to ($a_1$) may be utilized to indicate aggregator 240 should switch from assuming an exercise state to assuming a non-exercise state.

Aggregator 240 may use one of these processes or other similar processes or a combination of multiple processes to analyze data from supervised classifier 230a and output time intervals where the user is engaged in a physical activity or exercise. For example, aggregator 240 may use a process of streak-based aggregation to determine the starting point of a physical activity or exercise, and then may further use a process of accumulator-based aggregation in determining whether the user has stopped performing the physical activity or exercise. In some embodiments, aggregator 240 may run multiple aggregators concurrently (for example, streak-based and accumulator-based aggregators) and identify the start or end of physical activity or exercise when any one of the multiple aggregators indicates that physical activity or exercise starts or ends.

In some examples, initial data from the sensor array may be re-analyzed by supervised classifier 230a as described above, further using the output of aggregator 240 as an input to machine learning algorithms. The predetermined constants may be shared or uniquely assigned for different exercises or different types of exercises (for example, repetitive exercises such as pushups may use different constants than non-repetitive exercises such as jogging).

Controller 220 may also be configured to automatically determine a type of physical activity the user is actively engaged in during the determined time intervals based on the physical activity attributes. In other words, controller 220 may determine which exercise the user is actively engaged in each time interval where it has been determined the user is engaged in a physical activity or exercise. This process may be referred to herein as recognition. The process of recognition optionally may follow the process of aggregation and/or some recognition may be performed in parallel with segmentation and/or aggregation. In some embodiments, controller 220 may be configured to automatically determine a type of physical activity the user is actively engaged in during the determined time intervals based on only the physical activity attributes corresponding to the determined time intervals. In other words, only the physical activity attributes received from sensor array 210 for periods of time that have been determined as periods of exercise are used to determine the type of physical activity.

Recognition of the type of exercise may be used in downstream applications including counting of exercise repetitions, computing the efficiency or power of an exercise, determining a user's caloric expenditure over the course of an exercise, etc. PAMD 200 may also be configured to analyze a user's physical activity attributes and further provide feedback to the user regarding the user's form or other information that may enhance the user's exercise experience. Controller 220 may be trained to recognize types of physical activities based on the user's physical activity attributes through a machine learning process. In some examples, PAMD 200 may indicate a specific activity to be performed by the user. In these examples, the process of recognition may be ignored, combined with, and/or reinforced by the process of segmentation.

Figure 5:
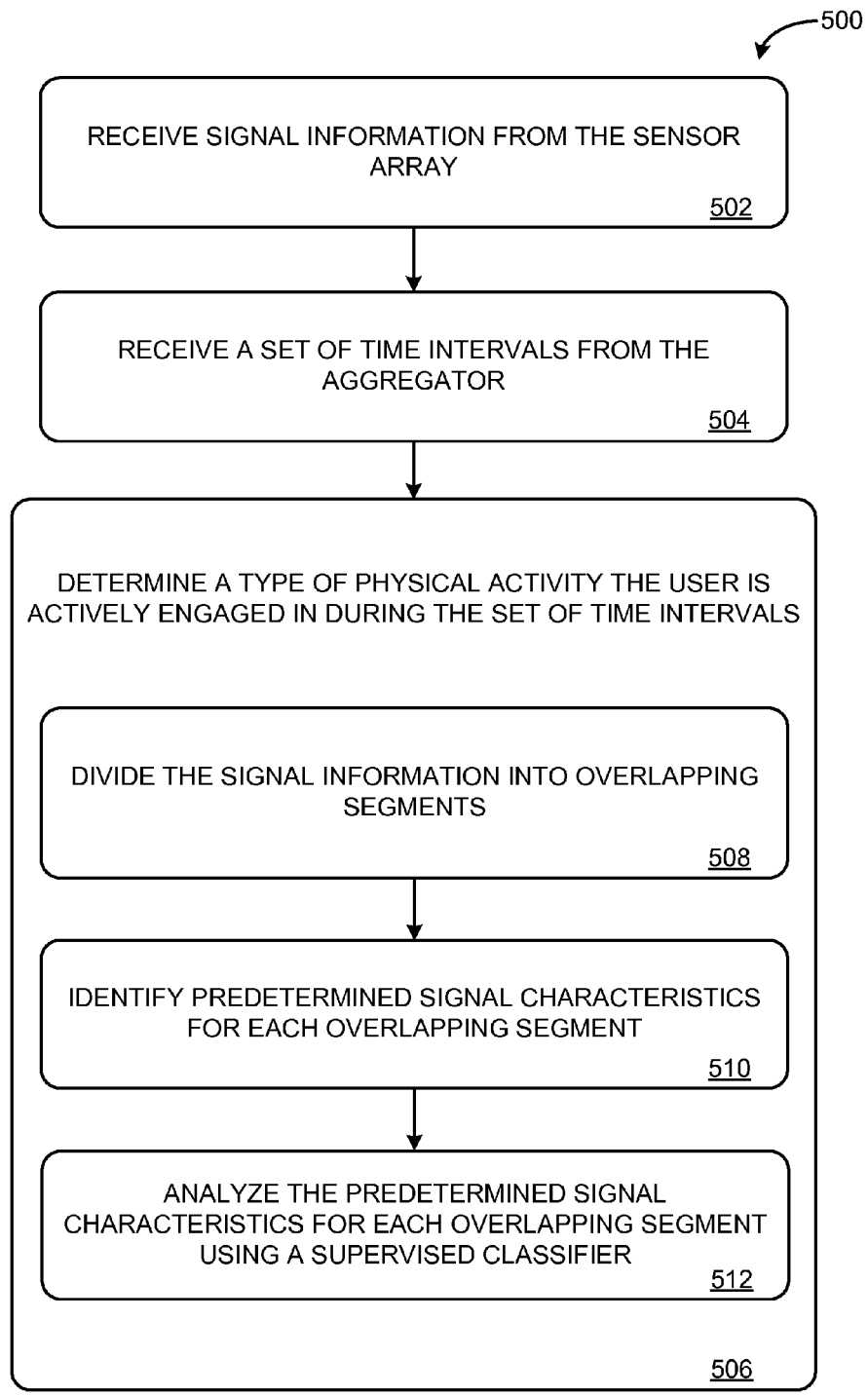
FIG. 5 shows an example method of recognizing a type of physical activity in accordance with an embodiment of the present disclosure.

FIG. 5 shows one example method 500 for recognition of a type of physical activity or exercise. At 502, method 500 may include receiving signal information from the sensor array (e.g., sensor array 210). Such signal information may be received by controller 220, for example. The signal information may include raw data from accelerometer 214 and gyroscope 216. The raw data may be further processed by a low-pass filter to yield smoothed accelerometer and gyroscope data. The signal information may also include the projection of the accelerometer signal onto the first principal component of that signal. The signal information may also include the projection of the gyroscope signal onto the first principal component of that signal.

At 504, method 500 may include receiving a set of time intervals from the aggregator (e.g. aggregator 240). Such a set of time intervals may be received by controller 220 and may be representative of time intervals in which the user is engaged in a physical activity or exercise. At 506, method 500 may include determining a type of physical activity the user is actively engaged in during the set of time intervals (e.g. recognition). In other words, the process of recognition may be applied when aggregator 240 indicates that the user is engaged in a physical activity or exercise.

The process of recognition may include a plurality of sub-processes. Nonlimiting examples of such sub-processes are provided below. However, it should be understood that recognition may be performed in any suitable manner without departing from the scope of this disclosure.

At 508, method 500 may include dividing the signal information into overlapping segments. In one example, the data may be divided into windows with a length of five seconds. Each window may be advanced by 200 ms from the previous window, such that each five second window shares 4.8 seconds of data with the previous and following windows.

At 510, method 500 may include identifying predetermined signal characteristics for each overlapping segment. In one example, each five second window of smoothed data may be transformed into a plurality of signal characteristics that are then used to characterize the physical activity or exercise. As one nonlimiting example, 60 signal characteristics may be used. For example, controller 220 may calculate 20 signal characteristics for each of the three axes of each of the overlapping segments. In this example, the signal characteristics include five evenly spaced autocorrelation bins, the root-mean-square amplitude, ten evenly spaced power bands, mean, standard deviation, kurtosis and interquartile range. Other signal characteristics may also be calculated for each of the three axes.

At 512, method 500 may include analyzing the predetermined signal characteristics for each overlapping segment using a supervised classifier (e.g. supervised classifier 230b). Supervised classifier 230b may be trained to recognize the type of physical activity the user is actively engaged in during the overlapping segment. Supervised classifier 230b may be trained through a process of machine learning to recognize signal characteristics that are representative of a particular type of physical activity or exercise.

In some examples, supervised classifier 230b may utilize a support vector machine (SVM) and/or a decision tree, as described above with reference to supervised classifier 230a. For example, analyzing the predetermined signal characteristics may include training the support vector machine with data collected from a plurality of users during time intervals where the users were engaged in a plurality of types of physical activity or exercise and generating a set of transformation vectors and a weight vector representative of a user engaged in a type of physical activity or exercise. Analyzing the predetermined signal characteristics may further include multiplying the predetermined signal characteristics by the set of transformation vectors and weight vector to obtain a plurality of multiplication products, comparing the multiplication products to data sets representative of each of a plurality of predetermined activities where the data sets have been predetermined through machine learning, and classifying overlapping segments as representative of a type of physical activity.

As shown in FIG. 2, PAMD 200 may further include voting machine 270. Voting machine 270 may be configured to determine the type of physical activity the user is likely to be actively engaged in during a time interval where aggregator 240 has determined that the user is engaged in a physical activity.

As discussed above with regard to segmentation, for a given time interval comprising a plurality of overlapping segments, the supervised classifier may output several predictions which disagree about which physical activity or exercise is being performed by the user. A voting scheme may be implemented by voting machine 270 to determine which physical activity or exercise the user is most likely engaged in. Voting machine 270 may output a physical activity or exercise for a given time interval, which may be reported to the user and, in the case of a repetitive exercise, which physical activity or exercise to use for counting.

In one example, voting machine 270 reports the output from a single window starting two seconds into a time interval where aggregator 240 has determined that the user is engaged in a physical activity. The physical activity attributes of the user at the beginning of an exercise period may be unreliable as the user may still be getting into proper form. Similarly, the physical activity of the user at the end of an exercise period may be unreliable as the user may be slowing down or deviating from proper form. In some examples, voting machine 270 may use a true voting scheme similar to the aggregating process described above. In some examples, voting machine 270 may alter its output during an exercise period if strong evidence is presented that the user is engaged in a different physical activity or exercise than initially reported.

At the end of the recognition voting stage, each time interval where aggregator 240 has determined that the user is engaged in a physical activity may be classified as representative of a type of physical activity or exercise. This information may be delivered to reporter 260 to output information regarding the type of physical activity.

PAMD 200 may be further configured to determine a number of repetitions the user performs of a repetitive physical activity or exercise. In other words, PAMD 200 may count the number of repetitions of an exercise performed by the user. This may allow for automatic tracking of activities for the user to review after completing a workout regimen. This may also allow for real-time goal assessment, where PAMD 200 may indicate the completion of a target number of repetitions. Counting may be implemented through a method including dimensionality reduction and peak-finding.

In one example, the counting process may assume that segmentation and recognition have already been performed by controller 220. The counting process may assume both start and end times of a physical activity or exercise have been determined. The process may also assume that the inputs include the classification of a time interval and the raw accelerometer sensor data between the start and end times. There may be types of physical activities or exercises where gyroscopic sensor data optionally may be used to improve the accuracy of the counting data. In some examples, the counting process may occur while the user is actively performing repetitions of a repetitive physical activity or exercise. In one example, the methods described herein may be utilized repeatedly on successively larger time intervals. In some examples, intermediate counting results may be used to reduce the number of counting iterations.

Figure 6:
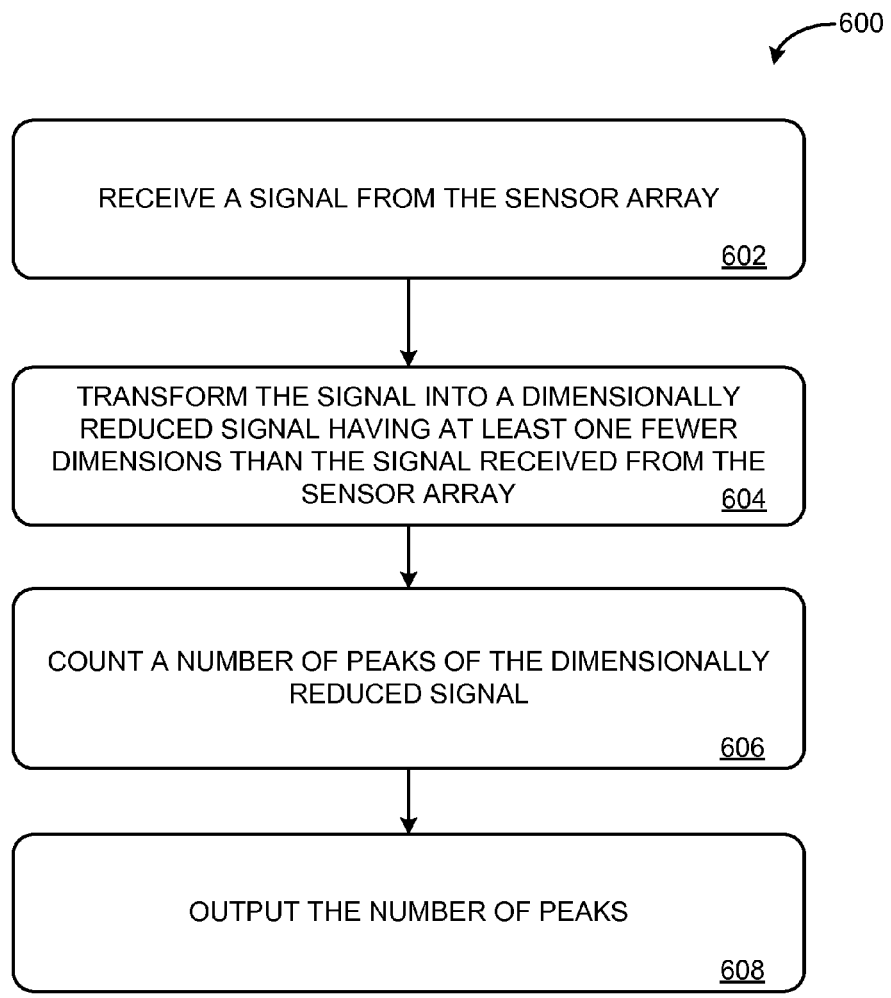
FIG. 6 shows an example method of counting exercise repetitions in accordance with an embodiment of the present disclosure.

FIG. 6 shows an example method 600 for counting the repetitions of a repetitive physical activity or exercise. At 602, method 600 may include receiving a signal from a sensor array (e.g. sensor array 210). Such signal information may be received by controller 220, for example. At 604, method 600 may include transforming the signal into a dimensionally reduced signal having at least one fewer dimensions than the signal received from the sensor array. At 706, method 700 may include counting a number of peaks of the dimensionally reduced signal. At 708, method 700 may include outputting the number of peaks.

In one example, the counting method may be divided into two stages. In the first stage, the raw sensor data is received by controller 220 from sensor array 210 and processed into a smooth one-dimensional signal. The processing may be such that the one-dimensional signal contains roughly the same number of peaks or cycles as the number of repetitions of a physical activity or exercise. The second stage includes counting the number of peaks of the one-dimensional signal. This peak count may be output as the repetition count.

The processing of the raw sensor data into a smooth one-dimensional signal may be referred to herein as the signal computation stage. The signal computation stage may include applying a bandpass filter to the raw data. The bandpass filter may be used to remove high frequency sensor noise as well as low frequency changes in the signal, such as changes due to the constant acceleration of gravity, for example. The bandpass filter may output frequency content relevant to counting repetitions.

The signal computation stage may further comprise subtracting the mean from the data. This may remove any remaining constant bias in the signal remaining after the bandpass filtering.

The signal computation stage may further comprise applying principal component analysis (PCA) to the filtered data. The implementation of PCA herein is similar to the application of PCA for segmentation described above, but for the counting process, the PCA is computed for the entire duration of a physical activity or exercise, as opposed to a fixed-sized overlapping segment. The smooth one-dimensional signal may be the result of the filtered data being projected onto the first principal component found by PCA.

In the example where PAMD 200 is a device worn on the wrist of the user (as shown in FIG. 1), the use of PCA may take advantage of the fact that for most exercises, most of the arm motion of the user can be summarized by motion along a single axis. For a shoulder press, for example, the axis would be the vertical or up-and-down axis. By projecting the signal data onto this axis, the dimensionality of the signal received from accelerometer 214 is reduced from three dimensions to one dimension. The PCA projection may now be such that a signal peak roughly corresponds to a repetition.

The counting method of this example may next proceed to the counting stage. In some examples, each repetition will correspond to a single strong peak, where each of the peaks are of similar shape and amplitude, and occur at a relatively constant frequency. In these examples, counting the strong peaks may be accomplished with any number of standard signal processing techniques. However, not every signal will fit these parameters. There may be multiple peaks per repetition, there may be large variation in the shape or amplitude, and the peaks may occur at an erratic frequency.

A heuristic peak counting method may thus be used in order to increase counting accuracy across a broad range of signal data. In one example the method proceeds in multiple stages. In one example, the method includes determining a set of candidate peaks, filtering the set of candidate peaks using local period estimates, filtering the set of candidate peaks using amplitude statistics, counting the number of peaks from the set of candidate peaks and outputting the number of peaks.

In one example, the method utilizes estimates of the minimum and maximum time needed to perform one repetition of the exercise. These values may be referred to herein as minAllowedPeriod and maxAllowedPeriod. These values may be estimated from data on an exercise-specific basis. For example, the values for jumping jacks are different than the values for push-ups, because people tend to do jumping jacks at a different rate than push-ups.

The counting method may begin with the computation of a set of candidate peaks. The final set of peaks counted will be a subset of this set of peaks. To compute the candidate peaks, the local maxima in the signal may be determined. These local maxima may then be sorted based on amplitude. A local maximum may be accepted as a candidate peak so long as it is at least minAllowedPeriod seconds away from a closest already accepted candidate peak. If two peaks in the signal are very close together (e.g. only 200 ms apart), one of them may not be a "real" repetition of the exercise. This closeness threshold may be set based on the fastest reasonable speed a human can perform a given exercise.

Counting peaks with a minimum separation may be done with a standard signal-processing operation, such as the Matlab findpeaks function with the MINPEAKDISTANCE parameter set to minAllowedPeriod or other equivalent signal processing operation. In this example, these candidate peaks are the input into the next step of the counting method.

As discussed above, minAllowedPeriod is an estimate of the minimum time needed to perform one repetition based on the fastest repetition recorded of that exercise during the machine learning process. In most cases it is much smaller than the actual time the user spends per repetition. As such, there may be multiple candidate peaks per actual exercise repetition. In the following step, the actual exercise period around each candidate peak may be estimated, and this estimation may be used to refine the set of candidate peaks.

For example, for each candidate peak an autocorrelation may be calculated in a window centered on the peak. The size of this window may be set to be two times maxAllowedPeriod or a predetermined duration (e.g., 9 seconds), whichever is smaller. The largest autocorrelation value within the range of lags [minAllowedPeriod, maxAllowedPeriod] may then be found. The lag at which the maximum autocorrelation value occurs may be an estimate of the exercise period for the candidate peak. Having computed these estimates, the filtering process described above may be repeated, with the exception that when considering whether to accept a candidate peak, minAllowedPeriod may not be used as the minimum allowed distance between the candidate peak and a previously selected peak. Rather, the minimum allowed distance may be set equal to ¾ the estimated period for that candidate peak, or another suitable ratio. This reduced set of candidate peaks may form the input to the next step of the counting method.

Next, the set of candidate peaks may be filtered based on peak amplitude. All of the candidate peaks may again be sorted based on amplitude, and the 40th percentile largest peak denoted (e.g. if there are 10 candidate peaks, the 4th-largest peak). All peaks that have amplitude less than half the amplitude of this peak may be disregarded. This method assumes that exercise repetitions should in general have large-amplitude peaks as they involve motion with high acceleration. Further, it may be assumed that within an exercise set all of the repetitions should have about the same amplitude. In other words, all peaks should be about as large as one of the largest peaks.

The sign of the one-dimensional signal found by PCA is arbitrary. However, this issue may be addressed in a number of ways. For certain exercises there may be a particular accelerometer axis which reliably corresponds to "up" and each repetition has one peak in this "up" direction. As an example, this may be the case for jumping jacks and the 'x' axis in a particular set of sensors. For these exercises, the PCA projection may be further manipulated such that the sign of the "up" axis in the projection is positive, allowing peaks to be counted in this example one-dimensional signal. Controller 220 may designate the number of peaks as the number of repetitions and the method may further comprise outputting the number of repetitions.

The counting method may be run twice, once to count peaks and once to count valleys. In one example, the method includes determining a set of candidate valleys, filtering the set of candidate valleys using local period estimates, filtering the set of candidate valleys, counting a number of candidate valleys from the set of candidate valleys, comparing the number of valleys to the number of peaks, designating the greater of the number of valleys and the number of peaks as a number of repetitions and outputting the number of repetitions.

In an example where the counting method is performed during the period where the user is actively engaged in a repetitive physical activity or exercise, it may be possible for the output of the peak counting method to decrease from one frame to the next, as the PCA axes may change over time and the criteria for amplitude-based rejection may shift over time as well. In order to prevent confusing the user with a decreasing repetition count, the method may not allow a count to decrease.

In some examples, the user may be performing a repetitive physical activity or exercise in pursuit of a target number of repetitions. In this example, the counting method may further include the steps of determining that the user has stopped performing a repetitive exercise based on the physical activity attributes, comparing the number of repetitions determined by the counting method to the target number of repetitions, and indicating that the user has completed the repetitive exercise when the number of repetitions determined by the counting method is within a threshold (e.g., two) of the target number.

Further, the physical activity monitoring device may be employed as part of a method of augmenting a gaming experience. This may allow a user to take a gaming console experience and extend it into the real world. A user may play a game inside the home, and the game may further incorporate an out of home (or otherwise untraditional) active gaming concept that employs a PAMD. This may allow a user to play a game in the real world, with the user's actions outside the immediate vicinity of the game console ultimately being used as an aspect of gameplay. For example, an avatar or game character controlled by the user may get stronger based on the number of calories burned by the user while the user runs for a determined time period or distance.

Figure 7:
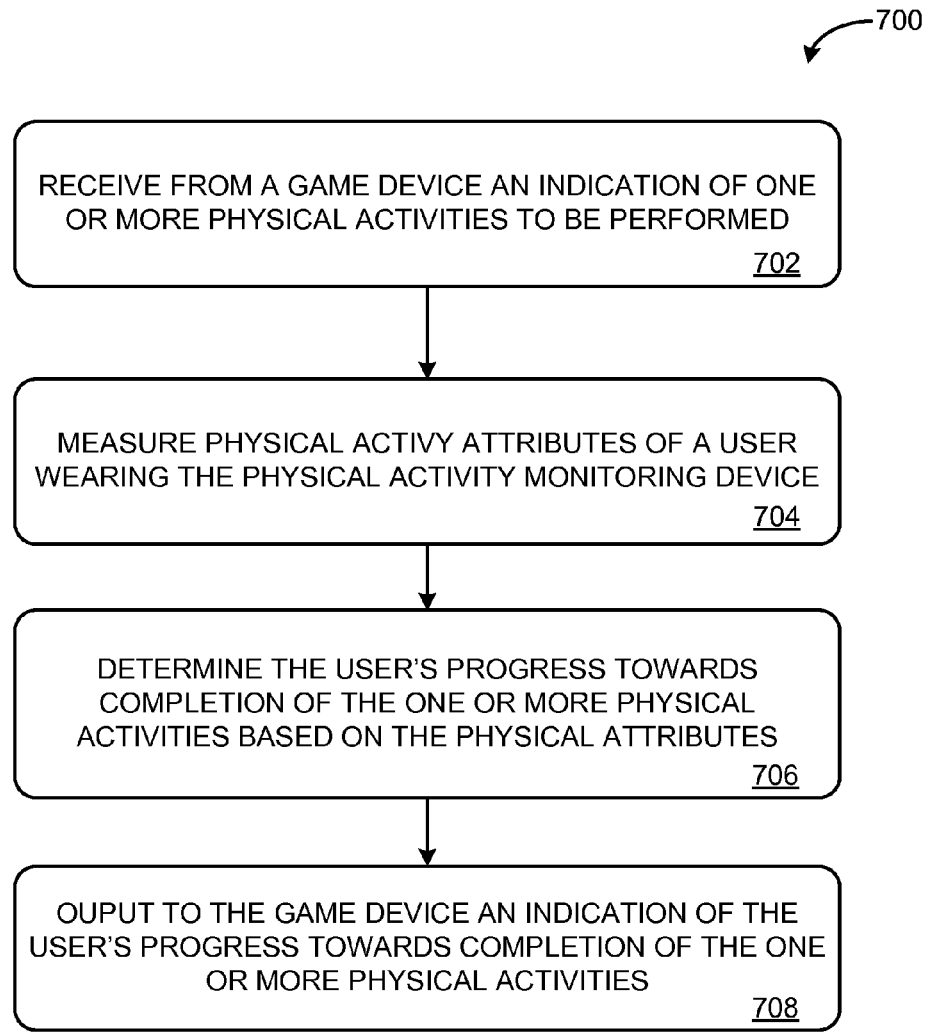
FIG. 7 shows an example method of augmenting a game experience in accordance with an embodiment of the present disclosure.

FIG. 7 shows one example method 700 of augmenting a game experience with use of a PAMD. At 702, method 700 may include receiving, at a PAMD from a game system, an indication of one or more physical activities to be performed. The physical activities may be performed as an extension of a game being played on the game system. For example, the game may tell the user to run outside, and the user may unlock gems at regular distance markers or calorie burn targets along the way that in turn increase the user's level in the gameplay inside the home. In some examples, the game may tell the user to do a predetermined number of pushups, further increasing the user's game score in the gameplay as the pushups are performed.

At 704, method 700 may include measuring physical activity attributes of a user wearing the physical activity monitoring device. As described above, the PAMD may be configured to automatically determine when a user is engaged in a physical activity or exercise, and further configured to automatically determine the type of physical activity or exercise being undertaken by the user. This may further allow the game system to assign a variety of physical activities or exercises to the user.

At 706, method 700 may include determining the user's progress towards completion of the one or more physical activities based on the physical attributes. As described above, the PAMD may be configured to count repetitions of a repetitive physical activity or exercise, and further configured to monitor the distance traveled by the user through signal information from a GPS and/or accelerometer. This may allow the PAMD to give the user tracking metrics and show the user's progress towards completion.

At 708, method 700 may include outputting to the game device an indication of the user's progress towards completion of the one or more physical activities. The PAMD may communicate to the game system as the user is performing the one or more physical activities, for example with communication subsystem 250. This may allow for in-game feedback to be delivered to the user from the game device. The PAMD and/or the gaming system may be further configured to sync data to a personal computer, mobile phone or other devices, allowing for data integration and recording.

Method 700 may further include indicating to the user information of the game as affected by progress towards completion of the one or more physical activities. This may allow the user to receive game feedback both while engaging with the game system and also while using the PAMD outside the vicinity of the game system. In one example, this may allow for the user to continue gameplay while earning achievements that affect their game score or other aspects of gameplay.

Method 700 may further include: at the physical activity monitoring device, calculating one or more current biometric markers for the user performing the one or more physical activities and/or indicating to the user one or more current biometric markers. The PAMD may be configured to give the user relevant feedback for fitness tracking with information regarding heart rate and personalized heart rate zones, GPS location information to view routes covered, distance, steps taken, duration of exercise, number of repetitions performed, time of day, an amount of calories burned by the user performing the one or more physical activities, and other relevant current biomarkers.

A PAMD in accordance with the present disclosure may be used by a user to track a workout and record fitness metrics. Furthermore, the PAMD may be configured to guide the user through a workout and monitor the user's progress during the workout. In other words, the physical activity monitoring device may serve as a physical trainer.

Figure 8:
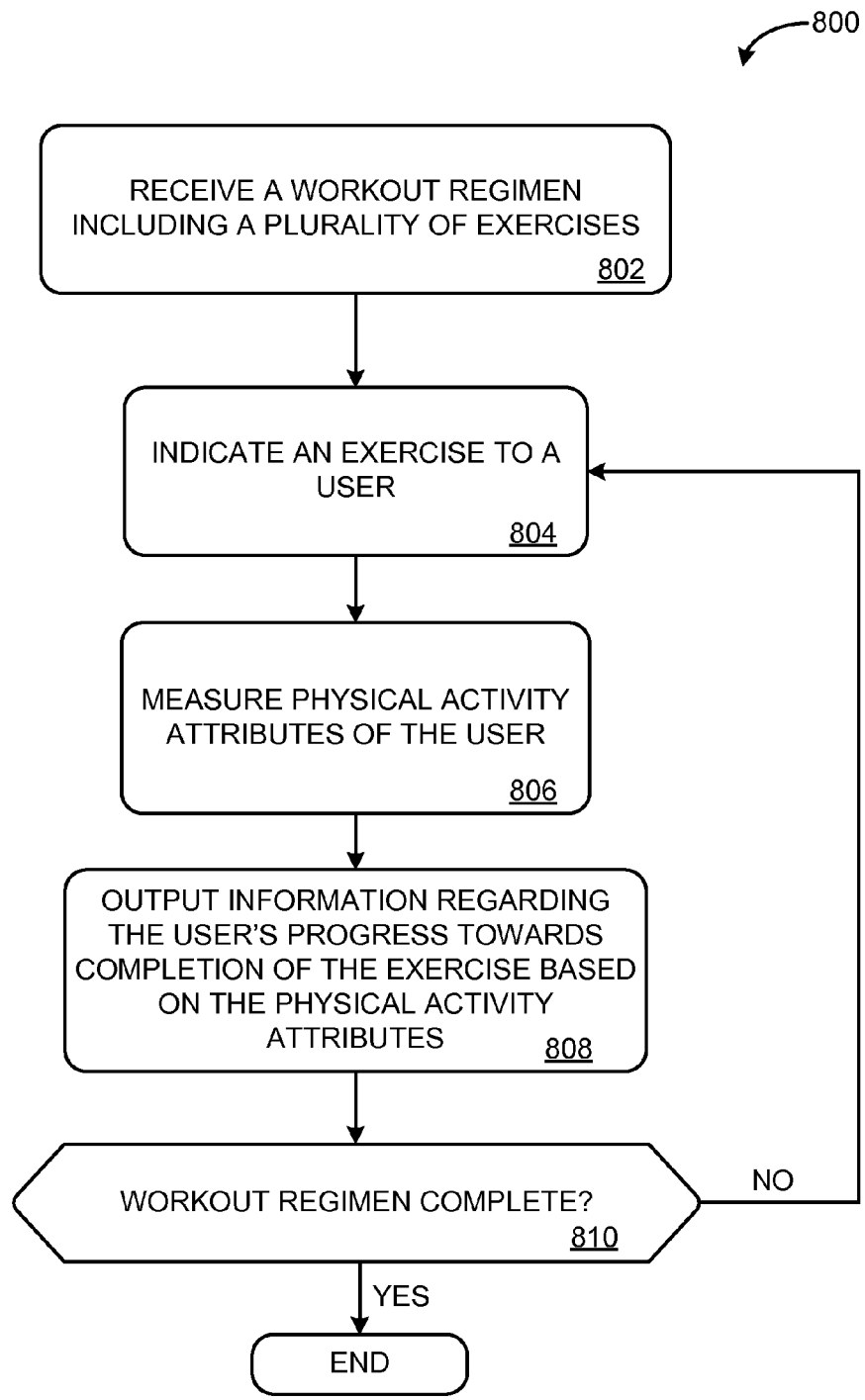
FIG. 8 shows an example method of physically training a user in accordance with an embodiment of the present disclosure.

FIG. 8 shows a method 800 of training a user of a PAMD. At 802, method 800 may include receiving at the PAMD a workout regimen including a plurality of exercises. In one example, the user may browse and select a workout on an app that runs on a personal computer, mobile phone, or gaming console, and have that workout regimen sent to the PAMD (e.g., via communication subsystem 250).

At 804, for each of the plurality of exercises included in a workout regimen, method 800 may include indicating an exercise to a user. The PAMD may include a display subsystem 280 and/or an audio subsystem that is configured to signify information that walks the user through the workout regimen step by step. For example, the user may select a workout on the PAMD and request to begin the workout. The PAMD may indicate to the user to do ten pushups, run two miles, etc.

At 806, method 800 may include measuring physical activity attributes of the user with the PAMD worn by the user as described above. At 808, method 800 may include outputting information regarding the user's progress towards completion of the exercise based on the physical activity attributes. For example, while the user performs pushups, the PAMD may recognize the activity and count the number of repetitions completed or the number of repetitions remaining for that exercise in the workout. The PAMD may dynamically display the number of repetitions, as well as display feedback regarding the user's heart rate, calories burned, time spent working out and other metrics relative to the workout or physical activity or exercise currently being performed by the user.

If the user completes an exercise as indicated by the PAMD, the method may further include: indicating to the user that an exercise has been completed. For example, if the user completes an exercise, an audible alarm or physical vibration may indicate that the user has completed the physical activity or exercise and that it is time to move on to the next physical activity or exercise in the workout regimen.

At 810, method 800 may include determining if the workout regimen has been completed. If the workout regimen includes unfinished exercises, method 800 may return to 804, where method 800 may include indicating a next exercise to the user. In one example, the information displayed by the display subsystem 280 may change to indicate the next exercise to the user. In some examples, the PAMD may give an audible cue to the user. If the workout regimen has been completed, the PAMD may end, and may further indicate the end of the workout to the user.

In some embodiments, the methods and processes described above may be tied to a computing system of one or more computing devices. In particular, such methods and processes may be implemented as a computer-application program or service, an application-programming interface (API), a library, and/or other computer-program product.

Returning to FIG. 2, physical activity monitoring device 200 includes a logic machine 215 and a storage machine 217 which may cooperate to instantiate controller 220, supervised classifier 230a, supervised classifier 230b, aggregator 240, communication subsystem 250, reporter 260, voting machine 270 and/or display subsystem.

Logic machine 215 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 215 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

Storage machine 217 includes one or more physical devices configured to hold instructions executable by the logic machine to implement the methods and processes described herein. When such methods and processes are implemented, the state of storage machine 217 may be transformed—e.g., to hold different data.

Storage machine 217 may include removable and/or built-in devices. Storage machine 217 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 217 may include volatile, nonvolatile, dynamic, static, read/write, read-only, random-access, sequential-access, location-addressable, file-addressable, and/or content-addressable devices.

It will be appreciated that storage machine 217 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 215 and storage machine 217 may be integrated together into one or more hardware-logic components. Such hardware-logic components may include program- and application-specific integrated circuits (PASIC/ASICs) or system-on-a-chip (SOC), for example.

Display subsystem 280 may be used to present a visual representation of data held by storage machine 217. This visual representation may take the form of a graphical user interface (GUI). As the herein described methods and processes change the data held by the storage machine, and thus transform the state of the storage machine, the state of display subsystem 280 may likewise be transformed to visually represent changes in the underlying data. Display subsystem 280 may include one or more display devices utilizing virtually any type of technology. Such display devices may be combined with logic machine 215 and/or storage machine 217 in a shared enclosure, or such display devices may be peripheral display devices.

Communication subsystem 250 may be configured to communicatively couple PAMD 200 with one or more other computing devices. Communication subsystem 250 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow PAMD 200 to send and/or receive messages to and/or from other devices via a network such as the Internet.

In examples where PAMD 200 contains a GPS and/or is configured to collect biometric data concerning the user, communication subsystem 250 may be configured to transmit data about the user to one or more other computing devices. In some examples, PAMD 200 and/or the one or more other computing devices may be configured to inform the user regarding data that may be collected and transmitted, and may be further configured to allow the user to provide consent to allow the PAMD to collect, transmit or otherwise share data regarding the user.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method of physically training a user, the method comprising:
   at a physical activity monitoring device including a sensor array including an accelerometer, receiving a workout regimen including a plurality of exercises;
   for each of the plurality of exercises:
      at the physical activity monitoring device, indicating the exercise to the user;
      with the physical activity monitoring device worn by the user, measuring physical activity attributes of the user;
      automatically determining time intervals where the user is actively engaged in the exercise based on the physical activity attributes at least in part by:
         acquiring signal information with the sensor array that is representative of the physical activity attributes of the user;
         dividing the signal information into overlapping segments;
         identifying predetermined signal characteristics for each overlapping segment; and
         analyzing the predetermined signal characteristics for each overlapping segment using a supervised classifier trained to recognize if the user is actively engaged in the exercise during the overlapping segment;

outputting information regarding the user's progress towards completion of the exercise based on the physical activity attributes; and if the workout regimen has not been completed, indicating a next exercise to the user.

2. The method of claim 1, further comprising: indicating to the user that an exercise has been completed.

3. The method of claim 1, further comprising: calculating one or more current biometric markers for the user performing the plurality of exercises.

4. The method of claim 3, further comprising: indicating to the user one or more current biometric markers.

5. The method of claim 4, where the one or more biometric markers include an amount of calories burned by the user performing the one or more physical activities.

6. The method of claim 1, where the supervised classifier includes a support vector machine, and where analyzing the predetermined signal characteristics further includes:

training the support vector machine with data collected from a plurality of users during time intervals where the users were engaged in a plurality of types of exercises;

generating a set of transformation vectors and a weight vector representative of a user engaged in a type of exercise;

multiplying the predetermined signal characteristics by the set of transformation vectors and weight vector to obtain a plurality of multiplication products;

comparing the multiplication products to data sets representative of each of a plurality of exercises where the data sets have been predetermined through machine learning; and classifying overlapping segments as representative of a type of exercise.

7. The method of claim 6, where the physical activity monitoring device further includes an aggregator configured to determine a time interval defined by a plurality of the classified overlapping segments where the user is likely to be actively engaged in an exercise.

8. The method of claim 1, further comprising:

for a repetitive exercise:
  indicating to the user a target number of repetitions of an exercise to be performed;
  determining a number of repetitions of the repetitive exercise performed by the user with a process that reduces a dimensionality of signals received from the sensor array.

9. The method of claim 8, where the number of repetitions is determined through a counting method that includes:

counting a number of peaks of the dimensionally reduced signal; and outputting the number of peaks.

10. The method of claim 9, where the counting method further includes:

determining a set of candidate peaks;
filtering the candidate peaks using local period estimates;
filtering the candidate peaks using amplitude statistics; and
outputting the number of peaks.

11. The method of claim 10, where the counting method further includes:

determining a set of candidate valleys;
filtering the candidate valleys using local period estimates;
filtering the candidate valleys using amplitude statistics;
counting a number of valleys of the dimensionally reduced signal;
comparing the number of valleys to the number of peaks; and
designating the greater of the number of valleys and the number of peaks as a number of repetitions; and
outputting the number of repetitions.

12. The method of claim 11, where the counting method further includes:

determining that the user has stopped performing a repetitive exercise based on the physical activity attributes;
comparing the number of repetitions determined by the counting method to the target number of repetitions;
indicating that the user has completed the repetitive exercise when the number of repetitions determined by the counting method is within two of the target number.

13. A physical activity monitoring device, comprising:

a communication subsystem configured to receive a workout regimen including a plurality of exercises;

a display subsystem configured to, for each of the plurality of exercises, indicate that exercise to a user;

a sensor array including one or more sensors configured to measure physical activity attributes of the user;

a controller trained with a machine learning process to automatically determine time intervals where the user is actively engaged in that exercise based on predetermined signal characteristics for overlapping segments of signal information from the sensor array, and to automatically determine the user's progress towards completion of that exercise based on the predetermined signal characteristics physical activity attributes; and a reporter configured to output information regarding the user's progress towards completion of that exercise.

14. The physical activity monitoring device of claim 13, further comprising a supervised classifier.

15. The physical activity monitoring device of claim 14, where the supervised classifier includes a support vector machine.

16. A method of physically training a user with a physical activity monitoring device worn by the user, the physical activity monitoring device including a sensor array including one or more sensors, the method comprising:

at the physical activity monitoring device, receiving a workout regimen including a plurality of exercises;
for each of the plurality of exercises:
  at the physical activity monitoring device, indicating the exercise to the user;
  with the sensor array, measuring physical activity attributes of the user;
  at the physical activity monitoring device, automatically determining time intervals where the user is actively engaged in the exercise based on predetermined signal characteristics for overlapping segments of signal information from the sensor array;
  at the physical activity monitoring device, automatically determining the user's progress towards completion of the exercise based on the predetermined signal characteristics;
  outputting information regarding the user's progress towards completion of the exercise; and
  if the workout regimen has not been completed, indicating a next exercise to the user.

* * * * *